US009050392B2

(12) United States Patent
Bourges et al.

(10) Patent No.: US 9,050,392 B2
(45) Date of Patent: Jun. 9, 2015

(54) HYDROGEL AND BIOMEDICAL APPLICATIONS THEREOF

(75) Inventors: Xavier Bourges, Mogneneins (FR); Serge Baroth, Reze (FR)

(73) Assignee: Biomatlante, Vigneux de Bretagne (FR)

( * ) Notice: Subject to any disclaimer, the term of this patent is extended or adjusted under 35 U.S.C. 154(b) by 997 days.

(21) Appl. No.: 12/515,059

(22) PCT Filed: Nov. 16, 2007

(86) PCT No.: PCT/EP2007/062470
§ 371 (c)(1),
(2), (4) Date: Sep. 17, 2009

(87) PCT Pub. No.: WO2008/059058
PCT Pub. Date: May 22, 2008

(65) Prior Publication Data
US 2010/0021544 A1    Jan. 28, 2010

(30) Foreign Application Priority Data
Nov. 17, 2006    (FR) ..................... 06 10064

(51) Int. Cl.
*A61L 27/52* (2006.01)
*A61K 9/00* (2006.01)
*A61K 41/00* (2006.01)
*A61L 27/26* (2006.01)
*A61L 27/48* (2006.01)
*A61L 27/50* (2006.01)
*C08B 15/00* (2006.01)
*C08B 37/00* (2006.01)
*C08B 37/08* (2006.01)
*C08J 3/075* (2006.01)
*C08J 3/28* (2006.01)
*C08L 1/26* (2006.01)
*C08L 5/08* (2006.01)

(52) U.S. Cl.
CPC .............. *A61L 27/52* (2013.01); *A61K 9/0024* (2013.01); *A61K 41/0019* (2013.01); *A61L 27/26* (2013.01); *A61L 27/48* (2013.01); *A61L 27/50* (2013.01); *C08B 15/005* (2013.01); *C08B 37/0063* (2013.01); *C08B 37/0072* (2013.01); *C08J 3/075* (2013.01); *C08J 3/28* (2013.01); *C08J 2301/28* (2013.01); *C08L 1/26* (2013.01); *C08L 5/08* (2013.01)

(58) Field of Classification Search
None
See application file for complete search history.

(56) References Cited

U.S. PATENT DOCUMENTS

| 4,871,490 A | 10/1989 | Rosiak et al. |
| 5,470,578 A | 11/1995 | Aoki et al. |
| 5,717,006 A * | 2/1998 | Daculsi et al. ................ 523/115 |
| 6,425,949 B1 * | 7/2002 | Lemaitre et al. ................ 106/35 |
| 6,911,212 B2 * | 6/2005 | Gertzman et al. ............ 424/426 |
| 2004/0030262 A1 * | 2/2004 | Fisher et al. ................ 600/564 |

FOREIGN PATENT DOCUMENTS

| EP | 1080737 B1 | 4/2003 | |
| WO | 95/21634 A1 | 8/1995 | |
| WO | WO 01/30407 | * 5/2001 | .............. A61L 15/60 |

OTHER PUBLICATIONS

Nagaswa, N. et al., Radiation crosslinking of carboxymethyl starch, Carbohydrate Polymers, 2004;58:109-113.
Yoshii, F., et al., Hydrogels of polysaccharide derivatives crosslinked with irradiation at paste-like condition, Nuclear Instruments and Methods in Physics Research B, 2003;208:320.324.
Wach, R. A., et al., Radiation crosslinking of methylcellulose and hydroxyethylcellulose in concentrated aqueous solutions, Nuclear Instruments and Methods in Physics Research B, 2003;211:533-544.
Database WPI Week 200439, XP002439821.
Database WPI Week 200431, XP002439823.
Database WPI Week 200630, XP002439824.
Database WPI Week 200132, XP002439825.
Database WPI Week 200528, XP002439822.

* cited by examiner

*Primary Examiner* — David J Blanchard
*Assistant Examiner* — Sarah Chickos
(74) *Attorney, Agent, or Firm* — Pepper Hamilton LLP

(57) ABSTRACT

The invention relates to a method for preparing a cross-linked sterile and homogeneous hydrogel for injection, characterized in that it comprises the following steps: (a) preparing an aqueous solution containing a polymer derived from cellulose and at least one water-soluble polymer, the total polymer content ranging from 0.5 and 5 wt %, preferably from 1 to 4 wt % and more preferably from 1.5 to 3 wt %; (b) optionally adding sold particles; (c) pouring the resulting liquid mixture with the optional solid particles into a vessel and closing dais vessel using a water-tight and gas-tight system; and (d) exposing said vessel containing the liquid and the optional solid particles to a radiation dose of between 5 and 50 kGy, preferably between 20 and 30 kGy, and more preferably of about 25 kGy. The invention also relates to a hydrogel obtained according to the above method and to the use thereof in medical applications.

26 Claims, No Drawings

HYDROGEL AND BIOMEDICAL APPLICATIONS THEREOF

CROSS-REFERENCE TO RELATED APPLICATIONS

This application is the U.S. National Stage filing under 35 U.S.C. §371 of International Application Serial No. PCT/EP 2007/062470 filed Nov. 16, 2007, which claims priority under 35 U.S.C. §119(a) to French Application Serial No. 06/10064 filed Nov. 17, 2006, each of which is incorporated herein by reference in its entirety.

The present invention relates to novel crosslinked injectable homogeneous hydrogels obtained from a mixture of two or three water-soluble polymers.

Crosslinking of the polymers and sterility of the material are obtained simultaneously by means of β or γ irradiation. The polymer concentration and the dose of radiation have to be accurately adjusted, depending on the physical properties of each polymeric raw material. The hydrogels according to the present invention are suitable for biomedical applications.

The water-soluble polymers and the hydrogels are widely used in the medical field, notably as implantable biomaterials. They may be used alone or in association with other phases, such as particles (metal, mineral or organic particles) and/or active substances.

All the hydrogels have a similar structure of the gelatin type, although their physical properties may widely vary, depending on their three-dimensional lattices, on their concentrations, on their swelling rate and on their hydrophilicity.

Two general categories of hydrogels may be defined: (a) physical gels (pseudo-gels), in which the chains are interconnected via electrostatic forces, hydrogen bonds, hydrophobic interactions, or entanglements of chains. Such gels are non-permanent and may usually be converted into polymeric solutions by heating. (b) chemical gels (real, permanent gels), in which covalent bonds connect the chains.

The main advantage of the use of hydrogels for preparing biomaterials lies in the possibility of obtaining novel tissues having sufficient volume and cohesion, while being inert and/or biodegradable. The hydrogels may also be used in surface treatments, for example in order to obtain biomimetic surfaces, bandages, or systems for administrating drugs.

These hydrogels are generally obtained from liquid or viscous water-soluble polymers. Like for hydrogels, these liquid or viscous water-soluble polymers are generally used for obtaining a certain volume of tissues or for carrying solid particles, depending on the implantation site. In these solutions, the water fills up the space between the polymeric chains. The hydrosoluble polymers then disappear within a period of time which varies depending on the irrigation of the operated area by the body liquids as well as on the biodegradability of the actual gel.

In ocular surgery, the main role of hydrosoluble polymers is to increase the volume of the inner segment of the ocular chamber. Sodium hyaluronate and hydroxypropylmethylcellulose are two examples of water-soluble polymers commercially used for such applications.

The water-soluble polymers find another application with injection of sodium hyaluronate by arthroscopy. American patent U.S. Pat. No. 5,470,578 describes an anti-rheumatismal composition based on a glycosaminoglycan bound to a lipid. This product, the life time of which is about 6-9 months, makes articular lubrication possible.

Patent application WO 95/21634 describes an original bone substitute developed in 1992. It consists of hydroxypropylmethylcellulose (HPMC), associated with granules of biphasic calcium phosphate, the main role of the water-soluble polymer being to carry the granules during the injection. Several commercial products then appeared on the same principle. One of them, described in European Patent Application EP 1 080 737, carboxymethyl-cellulose plays the same role as HPMC.

Water-soluble polymers also find applications in cosmetic surgery. Many products exist in this field and are based on sodium hyaluronate and its derivatives, carboxymethylcellulose, polyacrylamide, polyvinyl-pyrrolidone, etc. . . .

Development of novel biomaterials is today focussed in the direction of composite materials. By mixing different kinds of water-soluble polymers, it is possible to obtain hydrogels having novel Theological properties (thixotropy, plasticity, hydrophilic character . . . ). Interestingly, biocompatibility of the mixture may also be improved relatively to that of each of the starting polymers.

Chemical reactions between water-soluble polymers may be conducted in order to obtain hydrogels via a chemical route, but radiation techniques may also be applied for obtaining hydrogels. Advantageously, the radiation techniques at the same time provide sterilization of the final product. The radiations create covalent bonds between the polymers; they modify the molecular weight, the hydrophilicity and the mechanical properties of the starting polymers, either by direct irradiation of the polymers or by grafting other polymeric units on the chains. Another advantage of this technique is related to the fact that no toxic polymerization initiator or non-biocompatible catalyst is used. Unfortunately, the fact that many uncontrolled modifications may occur during irradiation, in particular with polysaccharides, remains a major drawback of this technique. The main fact caused by irradiation on polysaccharides is degradation; the second being crosslinking of the polymer, depending on its chemical structure. Both processes may occur simultaneously and their yield determines the structure of the final product.

Interestingly, different water-soluble polymers do not react in the same way to irradiation. Carboxymethyl-cellulose (CMC) is more sensitive to irradiation than methylcellulose (MC) or hydroxymethylpropylcellulose (HPMC) because of the ionic character of carboxymethylcellulose.

The radiation dose and the concentration also play a significant role. Generally, for high concentrations of polymers, crosslinking easily occurs when the radiation dose is optimum, interactions between the polymeric chains being more numerous than in diluted systems. On the other hand, if the polymer concentration is insufficient, the degradation phenomenon assumes a larger proportion than crosslinking and the polymeric solution finally becomes totally liquid.

Many scientists have investigated the effect of irradiation on crosslinking of polymers. In particular the team of the Takaski Radiation Chemistry Research Establishment, managed by Kaetsu, as well as Hoffman and his colleagues of the Center of Bioengineering at Washington University, have triggered increasing interest in forming biomaterials by means of radiations, and for investigating the crosslinking phenomenon.

Recently, Nasagawa and Yoshii (*Carbohydrate Polymers* 2004, 58, 109-113; *Nuclear Instruments and Methods in Physics Research Section B: Beam Interactions with Materials and Atoms* 2003, 208, 320-324) have synthesized different hydrogels from starch derivatives, by using radiations and without the help of any additive. They have discovered that high concentrations of polymers in an aqueous solution (so-called "paste-like" conditions) promote crosslinking. On the other hand, at low concentrations, the crosslinking phenomenon does not occur and it is mainly a degradation which is observed as a drop in viscosity. The amount of polymers was not sufficient in this case for obtaining crosslinking.

Wach et al. (*Nuclear Instruments and Methods in Physics Research section B: Beam Interactions with Materials and Atoms* 2003, 211, 533-544) have described the first crosslinked hydrogel comprising two cellulose ethers, methylcellulose and hydroxyethylcellulose. Even in this case, the concentrations of polymers were very high.

Pekel et al. (*Carbohydrate Polymers* 2004, 55, 139-147) have investigated crosslinking by irradiation of hydroxypropylmethylcellulose alone in a solution. With irradiation of HPMC in aqueous solutions at reasonable concentrations (paste-like conditions), it was possible to obtain gel formation. The percentage of gel was increased by using high levels of radiations.

Various techniques were made available for describing an irradiated hydrogel. On of the main tools is the sol-gel analysis, which is based on gravimetric measurement of the solution and of the gel fraction after irradiation.

The method may easily be applied and gives access to the yield of the crosslinking reaction, as well as to the degradation rate and scission rate of the polymeric chains.

The calculations are usually based on the Charlesby-Pinner equation (Atomic Radiation and Polymers; Pergamon Press, Oxford (1960)), a more general version of which was developed subsequently (*Radiat. Phys. Chem.,* 1998, 51, 13; *Radiat. Phys. Chem.* 1991, 37, 499). As this was described by Rosiak, "the polymer lattice and the structure of the gel have a totally different behavior of the starting molecules or of the partly crosslinked molecules; if they are flexible, they may have rubber properties, they may swell. The dose required for reaching the gel point is Dg and the crosslinking density due to a stronger dose D is often expressed as a coefficient $\delta$ related to D and Dg; $\delta = D/Dg$. By continuing irradiation ($\delta > 1$) the fraction of polymers bound together in a lattice or in a gel increases (gel fraction—g), while the remaining soluble fraction decreases; $s+g=1$. The relationship between the soluble fraction s and the dose D depends on the initial distribution of the average molecular weights. The theory of the interaction of ionizing radiation with matter assumes that this crosslinking takes place randomly and proportionally to the dose."

An additional advantage related to the use of radiations is that with them it is possible to obtain a hydrogel as well as sterility of the product simultaneously whereas aseptic methods or additional sterilization steps are traditionally used for this purpose (steam, plasma, ethylene oxide, filtration . . . ).

By sterility is meant the condition of a material free of microorganisms.

According to the nature of medical material, one skilled in the art tries to obtain sterility by the most suitable and less degrading technique for the product. Aseptic methods and filtration are two methods which induce less modifications of water-soluble polymers. On the other hand, it is not possible to sterilize hydrogels and hydrosoluble polymers, by using ethylene oxide without any modification, because the gas rapidly reacts with water forming glycol.

U.S. Pat. No. 4,871,490 describes a hydrogel used as a bandage, obtained and sterilized by means of radiations in the form of thin swelled layers consisting of polyvinylpyrrolidone, polyethylene glycol and agar.

Polymers derived from cellulose have interesting properties for biomedical applications. They are soluble in water, chemically stable and non-toxic. Unfortunately, as mentioned above, they are more sensitive to radiations than the other types of polymers.

The irradiation technique has the attractive advantage of obtaining sterility at the same time as forming the gel. But the required "paste-like conditions", when polymers derived from cellulose are used, pose problem when the desired hydrogel is intended for injection.

The authors of the present invention have solved this problem and surprisingly found that a sterile and injectable gel based on a water-soluble polymer derived from cellulose, may be obtained by this technique, at very low concentrations.

The inventors have also found that crosslinking is more efficient when the polymer derived from cellulose is in the presence of other polymers which are less sensitive to radiations.

Further, the inventors have found that the amount and the concentration of polymers finally had to be adjusted in order to obtain the desired properties after irradiation, for example a liquid, viscous product, or in the form of a hydrogel.

The inventors have also found that the radiation dose should finally be adjusted in order to transform the polymers and at the same time sterilize the final product according to the standard.

More specifically, the invention relates to a method for preparing an injectable crosslinked sterile homogeneous hydrogel, characterized in that it comprises the following successive steps:

(a) preparing an aqueous solution comprising a polymer derived from cellulose and at least one second water-soluble polymer, the total polymer concentration being comprised by weight between 0.5% and 5%, preferably comprised between 1% and 4% and still more preferentially comprised between 1.5% and 3% of the total weight;

(b) optionally adding solid particles;

(c) pouring the resulting liquid mixture containing the optional solid particles, into a container and closing said container by means of a system impervious to water and to gas;

(d) exposing the container containing the liquid and the optional solid particles to a $\beta$ or $\gamma$ radiation dose comprised between 5 and 50 kGy, preferably comprised between 20 and 30 kGy, and still more preferentially about 25 kGy.

By $\beta$ radiation are meant $\beta$ rays consisting in the emission of $\beta$ particles, $\beta$ particles being electron or positron particles.

By $\gamma$ radiation are meant $\gamma$ rays which consist in electromagnetic waves having an energy larger than or equal to 10 keV. As an example of $\gamma$ radiations and in a non-limiting way, mention may be made of X-rays.

By hydrosoluble polymer derived from cellulose, is meant a cellulose polymer in which the hydroxyl groups have been replaced by various substituents. As an example of a polymer derived from cellulose and in a non-limiting way, mention may be made of hydroxypropylmethylcellulose (HPMC), methylcellulose (MC), hydroxyethylcellulose (HEC), hydroxypropyl cellulose (HPC) and carboxymethylcellulose (CMC).

By water-soluble polymer is meant a polymer soluble in water which is not toxic for mammals and in particular for humans.

The hydrogels according to the present invention may be used in tissular engineering. They may be injected with a syringe or a cannula.

The aqueous mixture may also fill a mold and then be exposed to radiations.

The water-soluble polymer derived from cellulose according to the invention may be selected from the group comprising hydroxypropylmethylcellulose (HPMC) and methylcellulose (MC).

According to an advantageous embodiment of the invention, the water-soluble polymer derived from cellulose is HPMC.

The second water-soluble polymer may be selected from the group comprising carboxymethylcellulose (CMC), glycosaminoglycans (GAG), polyvinylpyrrolidone (PVP), polyethylene glycol (PEG), polyvinyl alcohol (PVA) and sodium alginate.

According to an advantageous embodiment of the invention, the second hydrosoluble polymer is CMC.

Advantageously, the glycosaminoglycan (GAG) according to the invention may be selected from the group comprising sodium hyaluronate, hyaluronic acid, dermatan sulfate, keratin sulfate, heparin sulfate, chondroitin sulfate and chitosan.

According to an advantageous embodiment of the invention, the glycosaminoglycan is sodium hyaluronate.

According to another advantageous embodiment of the invention, the aqueous mixture comprises HPMC and CMC.

In another advantageous embodiment of the invention, the aqueous mixture comprises HPMC and sodium hyaluronate.

Advantageously in the method according to the invention:
- the water-soluble polymer derived from cellulose is hydroxypropylmethylcellulose at a weight concentration comprised between 0.5% and 2.5%, advantageously between 1% and 2%, and still more advantageously about 1.5% of the total weight; and
- the second water-soluble polymer is selected from the group comprising carboxymethylcellulose at a weight concentration comprised between 0.1% and 1%, advantageously between 0.25% and 0.7%, and still more advantageously about 0.5% of the total weight, or sodium hyaluronate at a weight concentration comprised between 0.1% and 1%, advantageously comprised between 0.25% and 0.7%, and still more advantageously about 0.5% of the total weight.

HPMC and MC are non-ionic polymers unlike CMC. During $\beta$ irradiation, the newly formed polymer from HPMC and CMC is ionic. Depending on the concentration of polymers, the formed product may be liquid, viscous or as a hydrogel. In our case, homogenous hydrogel is sought. The final product is a hydrogel when crosslinking has been very effective.

Advantageously, the aqueous mixture of water-soluble polymers further comprises at least one biocompatible polymer.

The biocompatible polymer may be selected from the group comprising polylactic acid, copolymers of polylactic acid and of polyglycolic acid, poly($\epsilon$-caprolactone), polyhydroxybutyrates, polyhydroxyvalerates, copolymers of polyhydroxybutyrates and polyhydroxyvalerates, polyurethanes, cellulose, polyethylene, polycarbonates, polymethylmethacrylate, silicones, polyamides and polyglycolic acid.

The solid particles according to the invention may be selected from the group comprising biphasic calcium phosphate (BCP), tricalcium phosphate ($Ca_3(PO_4)_2$), hydroxyapatite ($Ca_{10}(PO_4)_6(OH)_2$), calcium sulfate, alumina zirconite, nasicon, bioglasses, vitroceramics, nanoparticles, radioopaque compounds as well as mixtures comprising several of these compounds.

Advantageously, the solid particles are BCP granules.

BCP is a mixture consisting of hydroxyapatite and $\beta$ tricalcium phosphate.

Advantageously, the hydroxyapatite/$\beta$ tricalcium phosphate ratio is comprised between 10/90 and 90/10, advantageously comprised between 20/80 and 80/20, advantageously about 60/40.

BCP is known as an osteoconductor and is widely used as a bone substitute. In the bone substitute according to the invention, the hydrogel plays the role of a spacer between the granules in order to allow cell colonization on the totality of the product during bone formation.

The amount of solid particles in the hydrogel is advantageously comprised by weight between 15% and 75%, advantageously comprised between 30% and 60% of the total weight.

According to an advantageous embodiment of the invention, the weight of the solid particles in the hydrogel represents about 55% of the total weight.

According to an advantageous embodiment of the invention, the weight of the solid particles in the hydrogel represents about 55% of the total weight.

Advantageously, the polymer derived from cellulose is HPMC and the water-soluble polymer is CMC or a GAG, said GAG advantageously being sodium hyaluronate and solid particles advantageously being BCP granules.

In a particularly advantageous embodiment of the invention, the aqueous mixture comprises HPMC, CMC and BCP granules.

According to advantageous embodiment of the invention, the mixture contains by weight:
- 45% of an aqueous mixture of hydroxypropyl-methylcellulose and carboxymethylcellulose;
- 44% of biphasic calcium phosphate granules with a diameter comprised between 80 and 200 µm in which the hydroxyapatite/$\beta$ tricalcium phosphate ratio is 60/40; and
- 11% of biphasic calcium phosphate granules with a diameter comprised between 0.5 and 1.0 mm in which the hydroxyapatite/$\beta$ tricalcium phosphate ratio is 60/40.

According to another advantageous embodiment of the invention, the aqueous mixture contains by weight:
- 45% of an aqueous mixture of hydropropylmethyl-cellulose with a weight concentration of 1.5% and of carboxymethylcellulose with a weight concentration of 0.5%;
- 44% of biphasic calcium phosphate with a diameter comprised between 80 and 200 µm in which the hydroxyapatite/$\beta$ tricalcium phosphate ratio is 60/40; and
- 11% of biphasic calcium phosphate granules with a diameter comprised between 0.5 and 1.0 mm in which the hydroxyapatite/$\beta$ tricalcium phosphate ration is 60/40.

Active substances may be added to the hydrogels of the invention after irradiation.

By active substances are meant molecules having pharmaceutical or cosmetic activity.

The active substance may be selected in a non-limiting way from the group comprising antibiotics, growth factors, hormones, peptides, anti-osteoporosis agents and anti-tumoral agents.

As an example of containers suitable for applying the method according to the invention and in a non-limiting way, mention may be made of syringes, cannulas or molds. These containers may be in glass, in stainless steel or in silicone.

The method according to the invention may comprise an optional step (e) consisting of dehydrating hydrogel obtained at the end of step (d).

Advantageously, the weight ratio of cellulose-derived polymer/second water-soluble polymer is comprised between 65/35 and 85/15, more advantageously between 70/30 and 80/20, still more advantageously equal to about 75/25.

The object of the invention is also hydrogels which may be obtained according to the method described earlier.

Hydrogels according to the invention which do not comprise solid particles may be used in a non-limiting way as a humidifying bandage for burns and bedsores, or as a membrane for reducing post-surgical adhesions after an abdominal or pelvian laparotomy.

The hydrogels according to the invention which do not comprise solid particles may also be used for filling wrinkles in cosmetic surgery or in order to give back volume to soft tissues.

The hydrogels according to the invention may further comprise solid particles in order to be used as bone substitutes.

Several synthetic bone resorption substitutes are already available in solid form, as a cement or mastic according to the use for which they are intended, depending on the implantation site, as well as depending on bone regrowth kinetics.

The main advantage of synthetic bone substitutes over natural grafts is related to their innocuity, since they are free of viruses, prions or bacteria. Thus, if the self-graft is not available in a sufficient amount, the bone substitute may be added as a supplement. They have also shown their effectiveness in terms of osteoconduction as compared with self-grafts (reference standards) and may now be used alone.

The bone substitutes according to the invention may be used in vertebroplastic, instead of commonly used cement of the polymethyl methacrylate type (PMMA). The latter are biocompatible, but they do not allow natural bone resorption. Indeed, dislocation of the vertebrae close to the ones which are operated on, is often observed after a few years because of the rheological difference between the inside of natural vertebrae and that of vertebrae filled with PMMA cement. This problem is avoided by the use of a resorption material according to the present invention.

According to the present invention, the bone substitute may also be used in maxillo-facial surgery, in particular for treating bone defects, for filling sinuses, for filling dental alveolae in order to maintain the gingival crest height, in reconstruction of the mastoidal cavity.

The bone substitute according to the invention may further be used in orthopaedic surgery, in surgery for filling a tumoral cavity, for treating fractures with bone defects, against pseudo-arthrosis with or without any bone defect.

During bone resorption when applying bone substitutes according to the invention, the bone cells resorb and replace the biomaterial with newly formed bone having a high mineralization level. Resorption/apposition cycles occur like in traditional bone, and the bone volume gradually increases to the expense of the gel.

BCP associates stability of hydroxyapatite, which acts as a good adhesion support for osteogenic cells, with good properties for salting out ions of β tricalcium phosphate which promotes cell resorption.

The bone substitute according to the invention may further be used in fusion cages in vertebral arthrodesis (vertebral fusion). The cage may be filled with the polymeric mixture and during the sterilization step (by exposure to radiations), the gel is included in the cage.

The object of the invention is also the use of a hydrogel as defined earlier as a drug.

The object of the invention is also the use of a hydrogel as defined earlier as a bone substitute.

The object of the invention is also the use of a hydrogel as defined earlier for making a drug intended to treat bone defects or a drug intended to fill sinuses, or a drug intended to fill dental alveolae in order to maintain the gingival crest height, or a drug intended to reconstruct the mastoidal cavity.

The object of the invention is further the use of a hydrogel as defined earlier for making a drug intended to treat tumoral cavities, or a drug intended to treat fractures with bone defects, or a drug intended to treat pseudo-arthrosis with or without any bone defect.

The invention will now be illustrated in a non-limiting way by the following examples:

EXAMPLE 1

Hydrogel Prepared by Crosslinking of HPMC with CMC

Different solutions of HPMC E4M (Colorcon, France), were prepared with weight concentrations of 1%, 1.5%, 2% and 3% of the total weight in demineralized water. A solution of CMC BLANOSE® 7 HCF (water soluble polymer) (Cooper, France) at 2% in demineralized water was also prepared. The solutions were mixed for 16 hrs at room temperature and in different proportions, poured in 12 mL glass vials and closed with a bromobutyl plug. The vials were exposed to a dose of 25 kGy of β radiations in an industrial reactor (Ionisos, Chaumesnil, France). After irradiation, all the solutions were viscous with a viscosity comprised between 1,000 and 16,000 cP. The different mixtures obtained after irradiation were found in various forms depending on the proportions of polymers. The obtained results are reported in Table 1.

The textures of the obtained mixtures were very different, depending on the concentrations and proportions of polymers. With the presence of CMC, it was possible to obtain a homogeneous hydrogel in the case of sample 4 (HPMC 1.5%, CMC 0.5%); whereas for sample 2, HMPC alone at 1.5% led to a hydrogel with a non-homogenous texture.

Fourier transform infrared analyses detected the formation of carbonyl groups in the irradiated polymer. This phenomenon is known for cellulose and its derivatives.

pH measurements were carried out in sample 4: the pH was 5.5 before sterilization and reached 6.5 after irradiation. This change was ascribed to the transformation of the polymers: radicals form during irradiation and lead to the formation of polymers bearing novel ionic substituents along the cellulose chain, having an effect on the pH of the solution.

TABLE 1

| irradiation of HPMC and CMC solutions (β, 25 kGy) | | | |
|---|---|---|---|
| Samples | Polymeric mixtures | | Results |
| | HPMC 1% | CMC 2% | |
| 1 | 100 | 0 | Non-viscous liquid |
| | HPMC 1.5% | CMC 2% | |
| 2 | 100 | 0 | Non-homogeneous hydrogel |
| | HPMC 2% | CMC 2% | |
| 3 | 100 | 0 | Non-homogeneous hydrogel |
| 4 | 75 | 25 | Homogeneous hydrogel |
| 5 | 50 | 50 | Non-homogeneous hydrogel |
| 6 | 25 | 75 | Non-viscous liquid |
| 7 | 0 | 100 | Non-viscous liquid |
| | HPMC 3% | CMC 2% | |
| 8 | 100 | 0 | Homogeneous hydrogel |

EXAMPLE 2

Hydrogel Prepared by Crosslinking of HPMC with Sodium Hyaluronate

A solution of HPMC E4M (Colorcon, France) at 2% by weight in demineralized water was prepared. A sodium hyaluronate solution (HA-Na) (Cristalhyal, Soliance, France, Brookfield viscosity: 1,500 cP at 1% in solution) was also prepared at 2% by weight in demineralized water. The solutions were mixed for 24 hrs in different proportions, poured in 12 mL glass vials and closed with bromobutyl plugs. The vials were exposed to a dose of 25 kGy of β radiations in an industrial reactor (Tonisos, Chaumesnil, France). Before irradiation, all the solutions were viscous with a viscosity comprised between 1,000 and 16,000 cP. The mixtures obtained after irradiation had different textures, depending on the proportions of polymers. The results are reported in Table 2.

TABLE 2 irradiation of HPMC and HA-Na solutions (β, 25 kGy)

| Samples | HPMC 2% | HA-Na 2% | Results |
| --- | --- | --- | --- |
| 1 | 100 | 0 | Non-homogeneous hydrogel |
| 2 | 75 | 25 | Homogeneous hydrogel |
| 3 | 50 | 50 | Non-homogeneous hydrogel |
| 4 | 25 | 75 | Non-viscous liquid |
| 5 | 0 | 100 | Non-viscous liquid |

As observed for HPMC/CMC mixtures, the textures of the irradiation products were very different depending on the concentrations and proportions of polymers. The presence of HA-Na in the mixture allowed a homogeneous hydrogel to be prepared for the following composition: HPMC 1.5%, HA-Na 0.5% (m/m).

EXAMPLE 3

Bone Substitute Obtained from a Hydrogel According to the Invention and Calcium Phosphate Particles BCP granules were incorporated to water-soluble polymers according to the invention before irradiation.

In the BCP used, the hydroxyapatite/β tricalcium phosphate ratio is 60/40.

Surprisingly, it was seen that the proportion of BCP granules and of water-soluble polymers was crucial. If the mixture contained a too large amount of polymers, a non-homogeneous product was obtained after irradiation (one phase containing the granules and another phase without the granules).

On the other hand, if the mixture of polymers was not present in a sufficient amount, certain granules were not properly included into the hydrogel after irradiation.

Further, and in order to improve the mechanical strength of the bone substitute inside a closed cavity, two types of granules having different sizes were used: granules for which the diameter is comprised between 80 and 200 μm and granules of a diameter comprised between 0.5 and 1 mm. Thus, in the case of pressure on the product, the largest granules play the role of a plug for the smallest granules.

A particular formula with which a homogeneous product may be obtained was selected after a series of tests. The selected formulation comprises:

45% of an aqueous mixture of hydroxypropylmethyl-cellulose with a weight concentration of 1.5% and of carboxymethylcellulose with a weight concentration of 0.5%;

44% of biphasic calcium phosphate granules with a diameter comprised between 80 and 200 μm; and 11% of biphasic calcium phosphate granules with a diameter comprised between 0.5 and 1.0 mm.

The mixture was prepared in vacuo in order to obtain a product free of air bubbles, was directly poured in a straight glass syringe, a stainless steel cannula or a silicone mold which were sealed hermetically. The product was exposed to βradiations at a dose of 25 kGy, in order to provide a hydrogel including BCP granules.

The product obtained in a straight syringe or a cannula may easily be extruded. If the product is found in a straight mold, it may be extracted by hand by simple pressure. Moreover, this novel material may be used in open cavities, because the hydrogel including the BCP granules does not run.

EXAMPLE 4

Study of the Swelling Rate and of the Crosslinking Rate of Hydrogels versus the Beta Irradiation Dose As described earlier, depending on the irradiation dose, the swelling rate and the crosslinking rate may be modified. In order to verify this phenomenon, a study dealing with three mixtures of water-soluble polymers was carried out. The swelling rate and the crosslinking rate of hydrogels obtained versus the irradiation dose were analyzed.

The first mixture consists of HPMC (E 4 M, Colorcon) and CMC (BLANOSE® 7 H, Hercules) (water soluble polymer) with respective weight concentrations of 1.5% and 0.5% in solution in deionized water.

The second mixture consists of HPMC (E4M, Colorcon) and of sodium hyaluronate (Crystalhyal, Soliance) with respective weight concentrations of 1.5% and 0.5% in solution in deionized water.

The third mixture consists of HPMC (E4M, Colorcon ) and sodium alginate (Sigma Aldrich) with respective weight concentrations of 1.5% and 0.5% in solution in deionized water.

The polymer solutions were prepared with magnetic stirring and then filtered on 5 μm filtering cartridges. The solutions were then conditioned in 20 mL borosilicate glass flasks and closed with bromobutyl plugs. The latter were then exposed to different doses of β irradiation at the Tonisos Centre in Chaumesnil (France). The doses were the following: 10, 15, 20, 37.5 and 50 kGy. For all the irradiation doses, formation of a hydrogel was observed.

In order to determine the swelling rate, the following procedure was established. About 5 g of hydrogel (m0) were exactly weighed and crushed with a pestle in the presence of 30 mL of deionized water. The hydrogel in the presence of water is left for 24 hrs in the oven at 37° C. in a beaker closed by parafilm. A control is directly dried at 100° C. in order to verify the percentage of dry polymers. After 24 hrs, the hydrogel is passed over a filter paper, it is recovered and weighed (mh). The swelling rate (Tg) is determined by the following formula $Tg=((mh-m0)/m0) \times 100$. During the swelling phase, the non-crosslinked polymeric phase disperses in water. In order to determine the crosslinking rate, the swollen hydrogel is dried in the oven at 100° C. for 24 hours. The dry mass of dried product is measured (ms), the crosslinking rate (Tr) is calculated in the following way: $Tr=(ms/(m0 \times 0.02)) \times 100$. The tables below show the results obtained on three types of hydrogel.

TABLE 3 swelling rate and crosslinking rate for the hydrogel (HPMC-CMC)
at different doses of beta irradiation.

|        | 10 kGy | 15 kGy | 20 kGy | 25 kGy | 37.5 kGy | 50 kGy |
|--------|--------|--------|--------|--------|----------|--------|
| Tg (%) | 369    | 261    | 231    | 245    | 236      | 245    |
| Tr (%) | 83.3   | 83.3   | 84.5   | 82.5   | 74.0     | 69.1   |

TABLE 4 swelling rate and crosslinking rate for the hydrogel (HPMC-sodium
hyaluronate) at different doses of beta irradiation

|        | 10 kGy | 15 kGy | 20 kGy | 25 kGy | 37.5 kGy | 50 kGy |
|--------|--------|--------|--------|--------|----------|--------|
| Tg (%) | 332    | 256    | 202    | 190    | 179      | 167    |
| Tr (%) | 78.4   | 82.2   | 82.7   | 78.8   | 71.8     | 67.7   |

TABLE 5 swelling rate and crosslinking rate for the hydrogel (HPMC-sodium
alginate) at different doses of beta irradiation

|        | 10 kGy | 15 kGy | 20 kGy | 25 kGy |
|--------|--------|--------|--------|--------|
| Tg (%) | 280    | 238    | 208    | 185    |
| Tr (%) | 77.9   | 78.5   | 78.4   | 79.2   |

It is observed that the swelling rate decreases with increasing irradiation doses for the three mixtures. Also it appears that the crosslinking rate remains unchanged between 10 and 25 kGy, and that the crosslinking percentage decreases from 37.5 kGy, this phenomenon being expressed by a larger degradation/crosslinking ratio. It is also seen that the swelling rate is not identical depending on the polymer associated with HPMC: this is explained by the intrinsic properties of each second polymer. With the mixtures of polymers it is possible to obtain controlled swelling rates versus the irradiation dose. Also, we have shown that the phenomenon was reproducible depending on the irradiation dose.

EXAMPLE 5

Biocompatibility Study of the Hydrogels and of
Bone Substitutes Prepared by Irradiation According
to the Invention 4.1. Products A hydrogel and a bone substitute were prepared according to Table 6. BCP was identical with the one used in the previous examples.

The HPMC was of the E4 M type (Colorcon, France), the CMC BLANOSE® H7 (water soluble polymer) (Cooper, France), the biphasic calcium phosphate granules were obtained from Biomatlante (France). Cytotoxicity was also tested on the BCP granules alone. In order to determine the effect of the radiation on cytotoxicity of the polymer, a fraction of the products was sterilized by steam (121° C., 20 minutes) and the other by b irradiation (25 kGy).

TABLE 6 hydrogel and bone substitute composition

|                | Polymer mixture<br>1.5% HPMC +<br>0.5% CMC | Particles<br>20% 80-200 μm +<br>80% 500-1000 μm |
|----------------|--------------------------------------------|-------------------------------------------------|
| Hydrogel       | 100                                        | 0                                               |
| Bone substitute| 45                                         | 55                                              |

The compositions of the tested products and their designation in the study are the following:
A Hydrogel, sterilized by irradiation
B Hydrogel, sterilized by steam
C Bone substitute, sterilized by irradiation
D Bon substitute, sterilized by steam
E BCP granules, sterilized by steam 4.2. Cell Line Osteoblasts of calvaria mice (MC3T3-E1) were used for this test.

4.3. Culture Medium

β-MEM was used as a culture medium. It was supplemented with 1% of penicillin/streptomycin, 1% of L-glutamine and 10% of fetal calf serum (FCS).

4.4. Tests

The tested samples were submitted to cytotoxicity evaluations in vitro, according to the standard of the International Standard Organization NF EN ISO 10993: Biological Evaluation of Medical Devices, Part 5: Tests for in vitro cytotoxicity.

The viability of the cells was measured by the MTS (Mitosis Tetrazolium Salt) test. This method is based on the mitochondrial capability of oxidizing tetrazolium salt in formazan. The intensity of the generated color is proportional to the activity of the mitochondrial dehydrogenase. The absorbance of formazan was measured at 490 nm, thereby giving access to cell activity.

4.5. Extraction Method

Samples comprising 0.2 g of a product A-E were immersed in 1 mL of supplemented α-MEM after sterilization. The samples were vigorously stirred for 2 min every 12 hrs and incubated for 48 hrs at 37° C. After incubation, the supplemented media were ultra-centrifugated (1,200 revolutions per minute for 8 minutes) and supernatants were put into contact with the cells. Different dilutions (1/10 and 1/100) were carried out from these supernatants (pure extracts).

4.6. Controls

Two controls were used:
a positive control in which the cells were cultivated on plastic wells with supplanted α-MEM.
a negative control in which the cells were cultivated on plastic with a supplemented medium plus 5 μg/mL of (cytolytic)D-actinomycin.

4.7. Results and Discussions

MC3T3-E1 cells were sown with 10,000 cells/cm$^2$ in plates of 96 wells. At a confluence of 90%, the culture medium was replaced by the pure extract and then diluted 10 and 100 times. At the same time, the cells were incubated in the presence of positive and negative controls.

Cytotoxicity was evaluated by measuring cell viability with the MTS test after 24, 48 and 72 hrs of incubation with the extracts. The results are shown in Table 7. They are expressed as a percentage of the MTS activity of the positive control. It is considered that cytotoxicity begins when the mitochondrial activity is reduced by more than 25% relatively to the positive control.

After 24 hrs of incubation, the MTS activity of the cells cultivated with the pure extracts was not significantly different from that of the positive control. The mitochondrial activity decreased by 14% for sample A, by 15% for B, by 4% for C, by 0% for D and by 3% for E. This suggests non-toxicity of the products.

TABLE 7 evaluation of the cytotoxicity of the hydrogels and bone substitutes

| Samples | Mitochondrial activity |
| --- | --- |
| Positive control | 100 |
| Negative control | 10 |
| A | 86 |
| A/10 | 92 |
| A/100 | 98 |
| B | 85 |
| B/10 | 95 |
| B/100 | 100 |
| C | 96 |
| C/10 | 95 |
| C/100 | 100 |
| D | 100 |
| D/10 | 100 |
| D/100 | 92 |
| E | 97 |
| E/10 | 95 |
| E/100 | 92 |

The cells in contact with the pure extracts diluted 10 and 100 times have not either any significant decrease in MTS activity, as compared with the positive control. The drop is 10% (for 10-fold dilution) and 2% (for 100-fold dilution) for A, 5% and 0% for B, 5% and 0% for C, 0% and 8% for D and 5% and 8% for E.

4.8. Conclusion

As a conclusion, the extracts of the tested materials did not show any evidence of cytotoxicity (reduction in cell viability by more than 25%) for none of the tested products under the conditions of this study. Further, no cytotoxicity difference was observed between products sterilized by irradiation and products sterilized by steam, both for the novel hydrogel and the novel bone substitute.

The invention claimed is:

1. A method for preparing an injectable crosslinked sterile homogenous hydrogel, wherein it comprises the following successive steps:
   (a) preparing an aqueous solution comprising a water-soluble polymer derived from cellulose and at least one second water-soluble polymer, wherein the total polymer concentration by weight is between 1% and 4% of the total weight;
   (b) adding bone substitute comprising solid particles;
   (c) pouring the resulting liquid mixture containing the solid particles, in a container, and closing said container by means of a system impervious to water and to gas; and
   (d) exposing the container containing the liquid and the optional solid particles to a dose of β or γ radiations comprised between 5 and 50 kGy, thus producing an injectable crosslinked sterile homogenous hydrogel;
   wherein the cellulose-derived polymersecond water-soluble polymer weight ratio is between 65/35 and 85/15.

2. The method according to claim 1, wherein the water-soluble polymer derived from cellulose is hydroxypropylmethyl cellulose or methyl cellulose.

3. The method according to claim 1, wherein the second water-soluble polymer is chosen from a carboxymethylcellulose, a glycosaminoglycan, a polyvinylpyrrolidone, a polyethylene glycol, a polyvinyl alcohol, and a sodium alginate.

4. The method according to claim 3, wherein the glycosaminoglycan is chosen from sodium hyaluronate, hyaluronic acid, dermatan sulfate, keratin sulfate, heparin sulfate, chondroitin sulfate, and chitosan.

5. The method according to claim 1, wherein:
   the water-soluble polymer derived from cellulose is hydroxypropylmethylcellulose at a weight concentration comprised between 0.5% and 2.5% of the total weight; and
   the second water-soluble polymer is carboxymethylcellulose at a weight concentration between 0.1% and 1% of the total weight, or sodium hyaluronate at a weight concentration between 0.1% and 1% of the total weight.

6. The method according to claim 1, wherein the aqueous solution of polymers further comprises at least one biocompatible polymer.

7. The method according to claim 6, wherein the biocompatible polymer is chosen from a polylactic acid, copolymers of polylactic acid and of polyglycolic acid, a poly(ε-caprolactone), a polyhydroxybutyrate, a polyhydroxyvalerate, copolymers of polyhydroxybutyrates and polyhydroxyvalerates, a polyurethane, a cellulose, a polyethylene, a polycarbonate, a polymethylmethacrylate, a silicone, a polyamide, and a polyglycolic acid.

8. The method according to claim 1, wherein the solid particles are chosen from biphasic calcium phosphate, β tricalcium phosphate, hydroxyapatite, calcium sulfate, alumina zirconite, alumina, nasicon, a bioglass, a vitroceramic, a nanoparticle, and a radio-opaque compound, or any mixture of the previous compounds.

9. The method according to claim 1, wherein the amount of solid particles is by weight between 15% and 75% of the total weight.

10. The method according to claim 1, wherein the aqueous mixture comprises by weight:
    45% of an aqueous mixture of hydroxypropylmethyl-cellulose and carboxymethylcellulose;
    44% of biphasic calcium phosphate granules with a diameter comprised between 80 and 200 μm wherein the hydroxyapatite/β tricalcium phosphate ratio is 60/40; and
    11% of biphasic calcium phosphate granules with a diameter comprised between 0.5 and 1.0 mm wherein the hydroxyapatite/β tricalcium phosphate ratio is 60/40.

11. The method according to claim 1, wherein an active substance is added after irradiation.

12. The method according to claim 11, wherein the active substance is chosen from an antibiotic, a growth factor, a hormone, a peptide, an anti-osteoporosis agent, and an anti-tumoral agent.

13. The method according to claim 1, wherein the container is an injection syringe or a cannula.

14. The method according to claim 1, wherein the cellulose-derived polymersecond water-soluble polymer weight ratio is between 70/30 and 80/20, or about 75/25.

15. The method according to claim 1, further comprising (e) dehydrating the hydrogel obtained in (d).

16. The method according to claim 1 wherein in (a), the total polymer concentration is by weight between 1.5% and 3% of the total weight.

17. The method according to claim 1 wherein in (d), the dose of β or γ radiations is between 20 and 30 kGy.

18. The method according to claim 2 wherein the water-soluble polymer derived from cellulose is hydroxypropylmethylcellulose.

19. The method according to claim 5 wherein the water-soluble polymer derived from cellulose is hydroxypropylmethylcellulose at a weight concentration between 1% and 2% of the total weight.

20. The method according to claim 5 wherein the second water-soluble polymer is carboxymethylcellulose at a weight concentration between 0.25% and 0.7% of the total weight, or sodium hyaluronate at a weight concentration between 0.25% and 0.7% of the total weight.

21. The method according to claim 8 wherein the solid particles are biphasic calcium phosphate.

22. The method according to claim 8 wherein the solid particles are comprised of hydroxyapatite and β tricalcium phosphate, wherein the hydroxyapatite/β tricalcium phosphate ratio is between 10/90 and 90/10.

23. The method according to claim 8 wherein the solid particles are comprised of hydroxyapatite and β tricalcium phosphate, wherein the hydroxyapatite/β tricalcium phosphate ratio is between 20/80 and 80/20.

24. The method according to claim 9 wherein the amount of solid particles is by weight between 30% and 60% of the total weight.

25. The method according to claim 3 wherein the glycosaminoglycan is sodium hyaluronate.

26. The method according to claim 14 wherein the cellulose-derived Polymer/second water-soluble polymer weight ratio is between 70/30 and 80/20.

\* \* \* \* \*